US012655454B2

(12) United States Patent (10) Patent No.: US 12,655,454 B2
Kwon et al. (45) Date of Patent: Jun. 16, 2026

(54) PROCESS FOR PRODUCING FORMATE USING OXYGEN-TOLERANT ENZYMES

(71) Applicant: GWANGJU INSTITUTE OF SCIENCE AND TECHNOLOGY, Gwangju (KR)

(72) Inventors: In Chan Kwon, Gwangju (KR); Jae Hyun Cha, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 290 days.

(21) Appl. No.: 18/391,941

(22) Filed: Dec. 21, 2023

(65) Prior Publication Data

US 2024/0209400 A1 Jun. 27, 2024

(30) Foreign Application Priority Data

Dec. 21, 2022 (KR) ........................ 10-2022-0180706
Dec. 7, 2023 (KR) ........................ 10-2023-0177033

(51) Int. Cl.
*C12P 7/40* (2006.01)
*C12N 9/02* (2006.01)

(52) U.S. Cl.
CPC .............. *C12P 7/40* (2013.01); *C12N 9/0067* (2013.01); *C12N 9/0093* (2013.01); *C12Y 112/99006* (2013.01); *C12Y 117/01* (2013.01)

(58) Field of Classification Search
CPC ....... C12P 7/40; C12N 9/0067; C12N 9/0093; C12Y 112/99006; C12Y 117/01
See application file for complete search history.

(56) References Cited

U.S. PATENT DOCUMENTS 10,801,052 B2 * 10/2020 Vincent ................... C12P 19/36
2024/0279691 A1 * 8/2024 Kim .......................... A61L 9/01

FOREIGN PATENT DOCUMENTS

KR 10-2022-0099312 A 7/2022

OTHER PUBLICATIONS

Adachi et al., Construction of a bioelectrochemical formate generating system from carbon dioxide and dihydrogen. Electrochem. Commun., 2018, vol. 97: 73-76. (Year: 2018).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Mourato et al., A continuous system for biocatalytic hydrogenation of CO2 to formate. Biores. Technol., 2017, vol. 235: 149-156. (Year: 2017).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Niks, Dimitri et al., "Chapter Eleven—Reductive activation of CO2 by formate dehydrogenases", Methods in Enzymology, 2018, vol. 613, pp. 277-295, DOI: 10.1016/bs.mie.2018.10.013.
Tanja Burgdorf et al., " [NiFe]-Hydrogenases of Ralstonia eutropha H16: Modular Enzymes for Oxygen-Tolerant Biological Hydrogen Oxidation", J Mol Microbiol Biotechnol, 2005, vol. 10, pp. 181-196, DOI: 10.1159/000091564.
Xuejun Yu et al., "Synthesis of Formate from CO2 Gas Catalyzed by an O2-Tolerant NAD-Dependent Formate Dehydrogenase and Glucose Dehydrogenase", Biochemistry, 2019, vol. 58, pp. 1861-1868, DOI: 10.1021/acs.biochem.8b01301.

* cited by examiner

*Primary Examiner* — Ganapathirama Raghu
(74) *Attorney, Agent, or Firm* — PLEECHAE IP, PLLC

(57) ABSTRACT

In a process for producing formate, a mixed enzyme by mixing hydrogenase (H₂ase) with oxygen tolerance and formate dehydrogenase (FDH) with oxygen tolerance is prepared, and the mixed enzyme and a gas including H₂, CO₂ and NAD⁺ are mixed such that formate may be produced even in the presence of oxygen, and thereby utilizing hydrogen sources including oxygen, such as coke oven gas.

6 Claims, 8 Drawing Sheets

Specification includes a Sequence Listing.

PROCESS FOR PRODUCING FORMATE USING OXYGEN-TOLERANT ENZYMES

CROSS-REFERENCE TO RELATED APPLICATION AND CLAIM OF PRIORITY

This application claims the benefit under 35 USC § 119 of Korean Patent Application Nos. 10-2022-0180705, filed on Dec. 21, 2022, and 10-2023-0177033, filed on Dec. 7, 2023, in the Korean Intellectual Property Office, the entire disclosure of which are incorporated herein by reference for all purposes.

BACKGROUND

1. Field of the Invention

The present invention relates to a process for producing formate.

2. Description of the Related Art

The development of renewable energy technologies to replace fossil fuels is essential for the sustainable growth of the economy and society. Hydrogen ($H_2$), obtained from various sources such as solar heat, algae, biomass, and by-product gas, is expected to be an alternative fuel with high gravimetric energy density and net-zero carbon dioxide ($CO_2$) production. However, due to the low volumetric energy capacity of $H_2$, its transportation and storage as a fuel are limited. Therefore, converting $H_2$ into a chemical with a high volumetric energy capacity while maintaining the molar energy capacity is required for the commercialization of alternative energy.

Suitable materials for converting $H_2$ energy should satisfy the following conditions: 1) high energy/volume capacity; 2) low energy loss during the conversion process; 3) liquid material at ambient pressure and temperature; and 4) non-flammable chemicals for safety. Formate satisfies these conditions, such that the conversion of $H_2$ and $CO_2$ into formate may be an appropriate approach for the commercialization of alternative energy. The oxidation of $H_2$ and reduction of $CO_2$ may occur in hydrogenase ($H_2$ase) and formate dehydrogenase (FDH), respectively, among oxidoreductases. However, synthetic catalysts for these reactions cannot be applied to various $H_2$ sources due to their low selectivity, low efficiency, and requirement for precious metals. In particular, cheap and sustainable $H_2$ sources, such as coke oven gas generated from steel industries, contain a small portion of $O_2$ (0.4 to 1.7%). Because of the transition metal active sites and low potential electrons, most $H_2$ases and FDHs are inhibited or irreversibly damaged by a trace amount of $O_2$, thereby limiting the application of $H_2$ in conversion into formate from various hydrogen sources.

SUMMARY

An aspect of the present invention is to provide a process for producing formate using oxygen-tolerant enzymes.

Another aspect of the present invention is to provide a process for producing formate utilising a hydrogen source including oxygen.

To achieve the above aspects, the following technical solutions are adopted in the present invention.

1. A process for producing formate including: preparing a mixed enzyme by mixing hydrogenase ($H_2$ase) with oxygen tolerance and formate dehydrogenase (FDH)

with oxygen tolerance; and mixing the mixed enzyme and a gas including $H_2$, $CO_2$ and nicotinamide adenine dinucleotide ($NAD^+$).

2. The process for producing formate according to the above 1, wherein the gas including $H_2$ contains $O_2$.

3. The process for producing formate according to the above 1, wherein the gas including $H_2$ is obtained from any one source selected from the group consisting of byproduct hydrogen incidentally generated in processes such as a petrochemical or steel industry, gas derived from plastic or solid waste, cokes, naphtha, volcanic gas, mineral water, coal gas, solar heat, algae emissions, biomass, natural gas, fossil fuel, coal, peat, petroleum and natural gasoline.

4. The process for producing formate according to the above 1, wherein the hydrogenase is derived from any one strain selected from the group consisting of *Ralstonia eutropha*, *Escherichia coli* and *Aquifex aeolicus*.

5. The process for producing formate according to the above 1, wherein the formate dehydrogenase is derived from any one strain selected from the group consisting of *Rhodobacter capsulatus*, *Desulfovibrio vulgaris*, *Clostridium carboxidivorans* and *Methylobacterium extorquens*.

6. The process for producing formate according to the above 1, wherein the hydrogenase includes the amino acid sequence of any of SEQ ID NO: 1 to SEQ ID NO: 5.

7. The process for producing formate according to the above 1, wherein the formate dehydrogenase includes the amino acid sequence of any of SEQ ID NO: 6 to SEQ ID NO: 8.

8. The process for producing formate according to the above 2, wherein the gas including H2 contains 5% or less of $O_2$.

9. The process for producing formate according to the above 2, wherein the gas including H2 contains 2% or less of $O_2$.

10. The process for producing formate according to the above 1, wherein the hydrogenase and the formate dehydrogenase are mixed in a ratio of 5 to 25:1.

The production process of the present invention enables the development of renewable energy to replace fossil fuels by converting $H_2$ into formate with a high volumetric energy capacity while maintaining the molar energy capacity.

The production process of the present invention enables the production of formate even in the presence of oxygen.

The production process of the present invention enables the production of formate using aerobic microorganisms or oxygen-tolerant enzymes derived from the microorganisms.

The production process of the present invention uses enzymes, thereby making it possible to produce $H_2$ and $CO_2$ into formate without by-products.

The present invention manufactures formate using enzymes, thereby enabling the reuse of the enzymes without loss of activity even after the production of the formate.

The production process of the present invention utilizes the hydrogen ($H_2$) source including oxygen, thereby making it possible to produce formate.

The production process of the present invention uses hydrogenases and formate dehydrogenases, thereby making it possible to produce formate from the hydrogen source including oxygen.

The production process of the present invention may adjust a ratio of hydrogenase and formate dehydrogenase, thus to easily increase the production of formate.

BRIEF DESCRIPTION OF THE DRAWINGS

The above and other aspects, features and other advantages of the present invention will be more clearly understood from the following detailed description taken in conjunction with the accompanying drawings, in which:

FIGS. 2A and 2B show SDS-PAGE of purified proteins ReSH and RcFDH stained with Coomassie blue, respectively. Wherein, MW represents a molecular weight marker, CL represents cell lysate after sonication, FT represents a flow-through streptavidin resin, and E represents an eluted protein;

FIGS. 6A to 5E show results of MALDI-TOF mass spectrometry for subunits of ReSH and RcFDH;

DETAILED DESCRIPTION OF THE INVENTION

Figure 1:
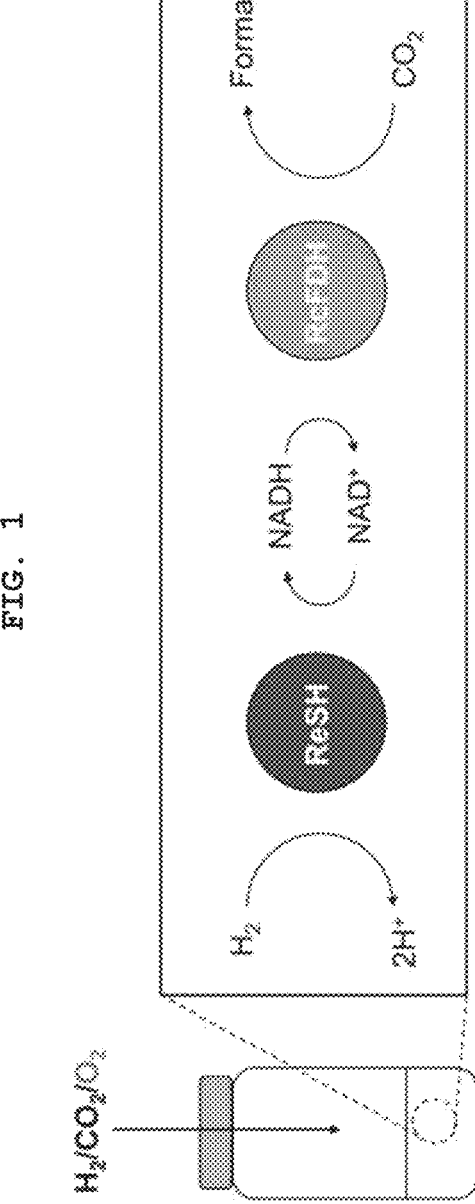
FIG. 1 is a schematic view showing the production process of formate through an $NAD^+$-dependent cascade reaction of ReSH and RcFDH in the presence of $O_2$.

The present invention provides a process for producing formate using oxygen-tolerant enzymes.

The present invention provides a process for producing formate using oxygen-tolerant enzymes, which includes preparing a mixed enzyme by mixing hydrogenase with oxygen tolerance and formate dehydrogenase with oxygen tolerance; and mixing the mixed enzyme and a gas including $H_2$, $CO_2$ and $NAD^+$, such that formate may be produced even in the presence of oxygen, and thereby utilizing hydrogen sources including oxygen, such as coke oven gas. That is, the present invention provides a process for producing formate, which is effective in solving the problem in that the production of formate was impossible due to the use of conventional hydrogenase and formate dehydrogenase, which are cheap and sustainable $H_2$ sources but contain $O_2$.

The present invention uses the mixed enzyme obtained by mixing hydrogenase with oxygen tolerance and formate dehydrogenase with oxygen tolerance. In the present invention, the oxygen tolerance means that the enzyme maintains activity without being deactivated even under a condition where oxygen is present.

The hydrogenase of the present invention refers to an enzyme that catalyzes the oxidation of hydrogen molecule ($H_2$). In the present invention, the oxidation of hydrogen through hydrogenase may be paired up with the reduction of an electron acceptor such as $NAD^+$ or Nicotinamide adenine dinucleotide phosphate ($NADP^+$), etc.

The hydrogenase of the present invention is not limited to those having a specific amino acid sequence or derived from a specific organism as long as they can catalyze the oxidation of hydrogen molecules while having oxygen tolerance.

In one embodiment, the hydrogenase of the present invention may be derived from aerobic microorganisms.

In one embodiment, the hydrogenase of the present invention may be derived from any one strain selected from the group consisting of *Ralstonia eutropha, Escherichia coli* and *Aquifex aeolicus.*

In one embodiment, the hydrogenase of the present invention may be [NiFe] $H_2$ase.

In one embodiment, the hydrogenase of the present invention may include a heterodimeric [NiFe] hydrogenase (HoxHY) subunit and a diaphorase (HoxFU) subunit.

In one embodiment, the hydrogenase of the present invention may include the amino acid sequence of any of SEQ ID NO: 1 to SEQ ID NO: 5.

In one embodiment, the hydrogenase with oxygen tolerance has activity under a condition where oxygen concentration is 10% or less, 9% or less, 8%; or less, 7% or less, 6% or less, 5% or less, 4% or less, 3% or less, 2% or less, 1% or less, 0.5% or less, or 0.1% or less.

In one embodiment, the oxygen tolerance of the hydrogenase of the present invention may be attributed to the reduction of $O_2$ bound to NiFe active site into either hydrogen peroxide or water.

Formate dehydrogenase of the present invention refers to an enzyme that catalyzes the reduction of carbon dioxide ($CO_2$) into formate. In the present invention, the reduction of carbon dioxide through formate dehydrogenase may be paired up with the oxidation of an electron donor such as NADH or Nicotinamide adenine dinucleotide phosphate (NADPH).

In the present invention, the formate dehydrogenase is not limited to those having a specific amino acid sequence or derived from a specific organism as long as they can catalyze the reduction of carbon dioxide into formate while having oxygen tolerance.

In one embodiment, the formate dehydrogenase of the present invention may be derived from aerobic microorganisms.

In one embodiment, the formate dehydrogenase of the present invention may be derived from any one strain selected from the group consisting of *Rhodobacter capsulatus, Desulfovibrio vulgaris, Clostridium carboxidivorans* and *Methylobacterium extorquens.*

In one embodiment, the formate dehydrogenase of the present invention may include the amino acid sequence of any of SEQ ID NO: 6 to SEQ ID NO: 8.

In one embodiment, the formate dehydrogenase of the present invention may include an FdsA subunit containing a bis(molybdopterin guanine dinucleotide) cofactor and an FdsGB diaphorase subunit.

In one embodiment, the formate dehydrogenase with oxygen tolerance has activity under a condition where oxygen concentration is 10%; or less, 9%; or less, 8% or less, 7% or less, 6% or less, 5% or less, 4% or less, 3% or less, 2.5% or less, 2% or less, 1.5% or less, 1% or less, 0.5% or less, 0.3% or less, or 0.1% or less.

In one embodiment, the oxygen tolerance of the formate dehydrogenase of the present invention may be attributed to the reduction of $O_2$ into hydrogen peroxide.

A mixing ratio of the hydrogenase with oxygen tolerance and the formate dehydrogenase with oxygen tolerance may be appropriately selected within a range where it is possible to produce formate, and is not limited to a specific ratio.

In one embodiment, the hydrogenase with oxygen tolerance and the formate dehydrogenase with oxygen tolerance may be mixed in a ratio of 0.1-50:1 (U/mL), such as 1-50:1, 5-50:1, 5-40:1, 5-30:1, 5-25:1, 5-20:1, 5-15:1, 10-40:1, 10-30:1, 10-20:1, 15-40:1, 15-35:1, 15-30:1, 15-25:1, 20-40:1 or 20-30:1.

The present invention uses a gas including $H_2$. The gas including $H_2$ of the present invention is not limited to a specific composition as long as it includes $H_2$, and is also not limited to one obtained from a specific source.

In one embodiment, the gas including $H_2$ may be obtained from any one source selected from the group consisting of byproduct hydrogen incidentally generated in processes such as a petrochemical or steel industry, gas derived from plastic or solid waste, cokes, naphtha, volcanic gas, mineral water, coal gas, solar heat, algae emissions, biomass, natural gas, fossil fuel, coal, peat, petroleum and natural gasoline.

In one embodiment, the gas including $H_2$ of the present invention may be coke oven gas produced from the steel industry.

In one embodiment, the gas including $H_2$ of the present invention may be byproduct hydrogen.

In one embodiment, the gas including $H_2$ of the present invention may be a gas derived from plastic or solid waste.

The gas including $H_2$ of the present invention may contain $O_2$. The gas including $H_2$ which contains $O_2$ of the present invention is not limited to a specific composition as long as it includes $H_2$ and $O_2$, and is also not limited to one obtained from a specific source.

In one embodiment, the gas including $H_2$ of the present invention may contain $O_2$ of 60% or less, 50% or less, 40% or less, 30% or less, 20% or less, 10% or less, 9% or less, 8% or less, 7% or less, 6%; or less, 5%; or less, 4% or less, 3% or less, 2% or less, 1% or less, 0.5% or less, or 0.1% or less based on a total weight of the gas.

EXAMPLE

1. Materials

The 5× In-Fusion HD Enzyme Premix was purchased from Takara Bio (Kusatsu, Japan). Strep-Tactin XT 4 Flow high-capacity resin was obtained from IBA Life Sciences (Gottingen, Germany). Disposable PD-10 desalting columns were purchased from Cytiva (Marlborough, MA, USA). Vivaspin 6 centrifugal concentrators with a molecular weight cutoff (MWCO) of 100 kDa were purchased from Sartorius (Göttingen, Germany). A polypropylene column (1 mL) was purchased from Qiagen (Hilden, Germany). The Ziptip $C_{18}$ resin was purchased from Millipore (Burlington, MA, USA). All other chemical reagents were purchased from Sigma-Aldrich (St. Louis, MO, USA) unless otherwise stated.

2. Experimental Method

2.1 Construction of Plasmids and Strains

To construct the Strep-Tag II-fused *Rhodobacter* capsulatu-derived formate dehydrogenase (RcFDH) expression plasmid, pTrcHis-RcFDH was used as a template. Injection cloning was performed to substitute the hexahistidine-tag for strep tag II. pTrcHis-RcFDH was amplified by PCR with the in-fusion primer (FW: SEQ ID NO: 9, RV: SEQ ID NO: 10). The PCR product was mixed with 5× In-Fusion HD Enzyme Premix to generate pTrcHis-strep-RcFDH. The *E. coli* MC1061 strain was transformed with pTrcHis-Strep-RcFDH, and *R. eutropha* HF210 [pGE771] strain was used as the *Ralstonia eutropha*-derived hydrogenase (ReSH)-expressing strain.

2.2 Expression of ReSH and RcFDH

For the expression of ReSH and RcFDH, a 7 L scale fermenter was used. First, a 10× H16 buffer (pH 7.0) containing 250 mM $Na_2HPO_4$ and 110 mM $KH_2PO_4$ was used as a medium. For 1 L of fructose-ammonium (FN) medium, 100 mL of 10×H16 buffer was mixed with 850 mL of sterile water (additional 13% (w/v) of Bacto agar in the case of solid agar plates) and autoclaved. Next, 10 mL of 20% (w/v) $NH_4Cl$, 1 mL of 20% (w/v) $NH_4Cl$, 1 mL of 20% (w/v) $MgSO_4*7H_2O$, 1 mL of 1% (w/v) $CaCl_2*H_2O$, 1 mL of 0.5% (w/v) $FeCl_3*6H_2O$ (in 0.1 N HCl), 1 mM $NiCl_2$, and 1.25 mL of 40% (w/v) D-fructose were mixed and filled up to 1000 mL with sterile $H_2O$. A single colony of *R. eutropha* was pre-cultured in 50 mL of FN medium containing 10 µg $mL^{-1}$ tetracyclin until the OD at 436 nm reached 1. For the main culture, 5 L of modified fructose-glycerol-ammonium ($FGN_{mod}$) with 0.05% (w/v) glycerol, 5 mL of SL6 trace element solution, and 5 mL of 1 mM $ZnCl_2$ (added to the FN medium containing 10 µg/mL tetracycline) were prepared in the fermenter. The pre-culture was inoculated into the $FGN_{mod}$ medium and subjected to 300 rpm shaking and 1 VVM aeration at 30° C. The pH range was maintained between 6.9 to 7.0 through automatic injection of 1 N NaOH. After 24 h, 5 mL of 1 mM $NiCl_2$ was added. When the OD at 436 nm reached 9-11, the cells were harvested by centrifugation at 6,000×g for 10 min, and stored at −80° C.

For RcFDH expression, a single-cell colony was pre-cultured in Luria-Bertani (LB) medium containing 150 µg $mL^{-1}$ ampicillin for 12 h at 37° C. For the main culture, 5 L of LB medium containing 150 µg $mL^{-1}$ ampicillin, 1 mM sodium molybdate, and 20 µM isopropyl β-D-1-thiogalac-topyranoside was prepared in the fermenter. The pre-culture was inoculated into the LB medium and subjected to 100 rpm shaking and 0.1 VVM aeration at 30° C. After 24 h, the cells were harvested by centrifugation at 6,000×g for 10 min, and stored at −80° C.

2.3 Purification of ReSH and RcFDH

Figures 2A, 2B:
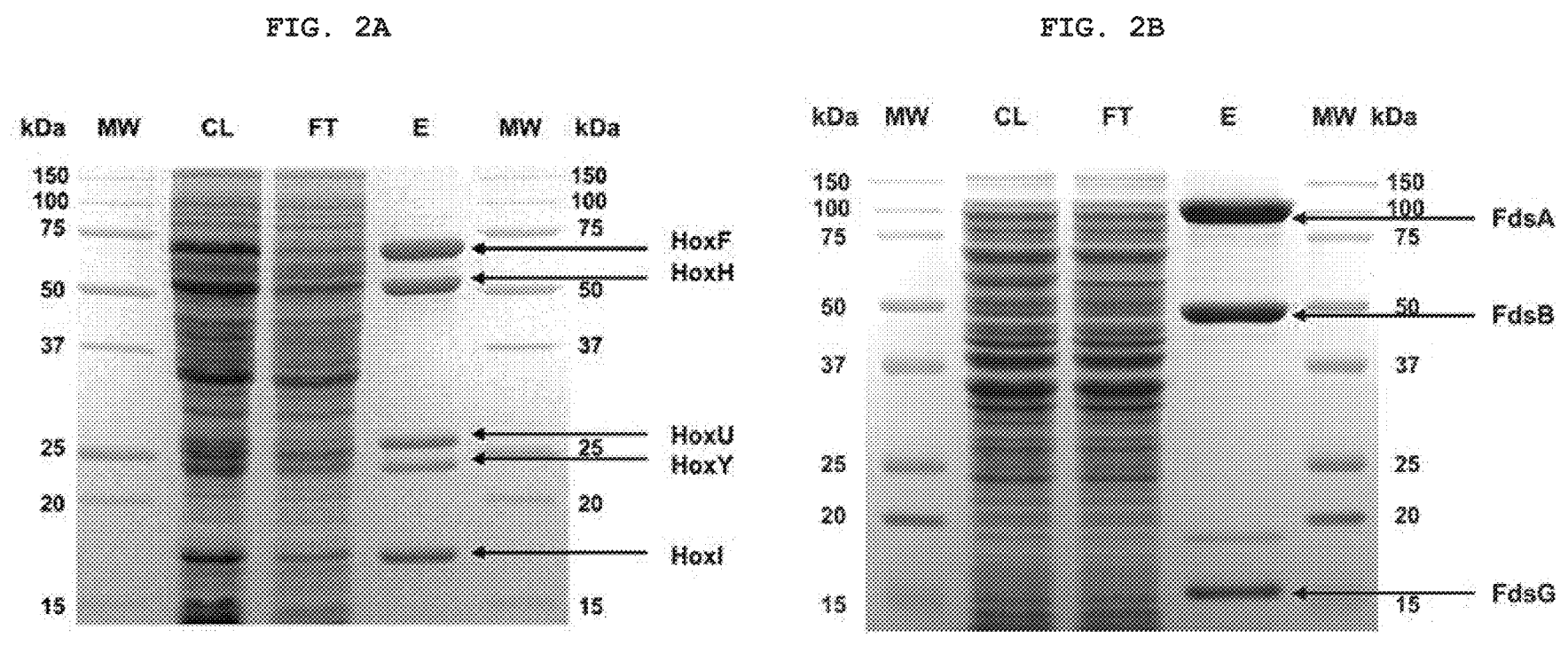

To purify ReSH and RcFDH, cell pellets were resuspended in 50 mM potassium phosphate buffer (pH 7.0) (Kpi buffer) containing 1 mg/mL lysozyme at a concentration of 1 g/10 mL. The resuspended cells were lysed by sonication (amplitude 28%, on/off 2 s/4 s) for 1 h. Insoluble cell debris was removed by centrifugation at 13,000×g for 30 min. Strep-Tactin XT 4 Flow high-capacity resin (2 mL) was mixed with the clear supernatants and incubated at 4° C. for 30 min. The resin was washed with Kpi buffer containing 300 mM potassium chloride on a gravity-flow polypropylene column to remove any impurities. The proteins were eluted with 3 mL of Kpi buffer containing 50 mM biotin, and buffer-exchanged with Kpi buffer containing 10 mM potassium nitrate using a PD-10 column. Protein purity was verified by SDS-PAGE (FIGS. 2A and 2B). The concentrations of the purified proteins were determined by measuring their absorbance at 280 nm using a microplate reader (Synergy, BioTek, Winooski, VT, USA). The extinction coefficients of ReSH and RcFDH were calculated to be 165, 710 and 350,000 $M^{-1}$, $cm^{-1}$, respectively, based on their amino acid sequences.

2.4 Matrix-Assisted Laser Desorption Ionization-Time of Flight (MALDI-TOF) Mass Spectrometry Proteins in buffer were desalted using Ziptip $C_{18}$ according to the manufacturer's protocol. The purified ReSH and RcFDH were mixed in a 1:1 (v/v) ratio with a sinapinic acid-saturated matrix solution consisting of 30% acetonitrile, 0.1% trifluoroacetic acid (TFA) and 70% water (v/v). The mixture was subjected to mass characterization by Autoflex speed (Bruker Corporation, Billerica, USA).

2.5 Enzyme Kinetics

The enzyme reaction kinetics of ReSH were measured for the NAD-dependent oxidation of $H_2$ to $H^+$ in the presence or absence of $O_2$. A sealing cuvette was filled with 900 µL of Kpi buffer containing $NAD^+$ and sealed; then, 100% $H_2$ and a mixed gas consisting of 10% $O_2$ and 90% $N_2$ (or 100% $N_2$ for anaerobic conditions) were injected simultaneously for 30 min at 10 mL/min. ReSH (2 mL, 80 nM) was purged with 10 mL/min $N_2$ gas bubbling in a 10 mL sealing vial for 30 min to remove $O_2$ from the air. The reaction was initiated by mixing 100 µL of 80 nM ReSH with a gas-saturated solution in the sealed cuvette. The final concentration of $NAD^+$ was varied from 0 to 2 mM.

The enzyme reaction kinetics of RcFDH were measured for NADH-dependent reduction of $CO_2$ to formate in the presence or absence of $O_2$. The sealing cuvette was filled with 900 µL of Kpi buffer containing NADH and sealed; then, 100% $CO_2$ and a mixed gas consisting of 4% $O_2$ and 96 $N_2$ (or 100% $N_2$ for anaerobic conditions) were injected simultaneously for 30 min at 10 mL/min, respectively. RcFDH (2 mL, 2 µM) was purged with 10 mL/min $N_2$ gas bubbling in a 10 mL sealing vial for 30 min to remove $O_2$ from the air. The reaction was initiated by mixing 100 µL of 2 µM RcFDH with a gas-saturated solution in the sealing cuvette. The final concentration of NADH was varied from 0 to 1 mM.

All measurements were performed in triplicate based on the change in the absorbance at 365 nm in the cuvette, measured using a T60 UV-Vis spectrophotometer (PG Instruments Ltd, Lutterworth, UK). The change in the absorbance over 1 min was plotted using the Michaelis-Menten equation to calculate the kinetic parameters.

2.6 Formate Production and Quantification

Figure 5:
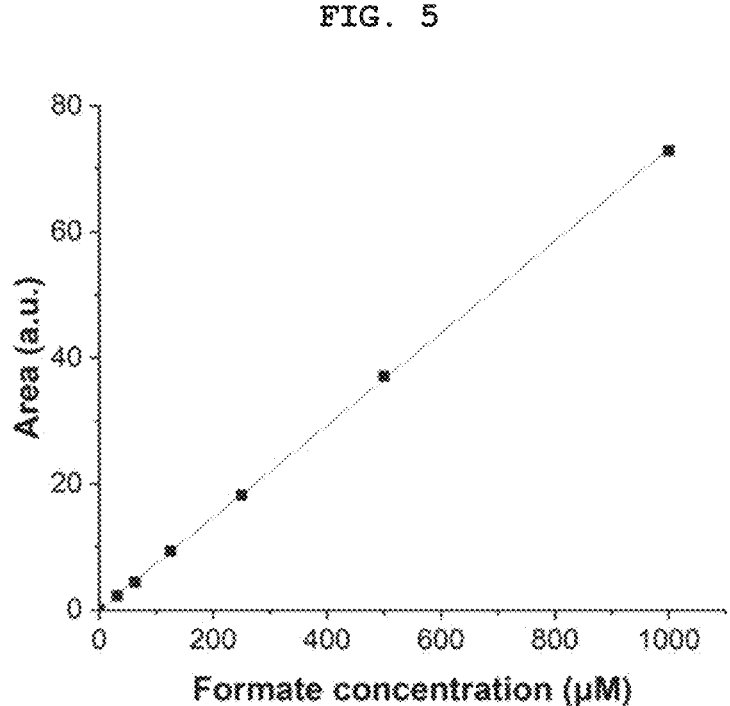
FIG. 5 shows a HPLC calibration curve of formate.

For the cascade reaction in the presence or absence of $O_2$, the gas content was controlled in a 20 mL polytetrafluoroethylene (PTFE) septa sealing vial. The vial was filled with 500 µL of reaction solution containing 3.2 U/mL ReSH, 0.16 U/mL RcFDH, 1 mM $NAD^+$ and 0.5 M Kpi buffer, and then sealed. A needle was inserted into the septa for gas evacuation. Then, 10 mL/min $CO_2$ and 20 mL/min $N_2/O_2$ mixed gas were injected for 30 min (the needle did not enter the reaction solution). The $O_2$ ratios of the mixed gas varied from 0 to 2-4%; therefore, the final concentrations of $O_2$ were 0, 1 and 2%. The reaction was initiated by a 10 mL/min $H_2$ gas injection. Formate production was sampled every 20 min during incubation for 1 h, and 10 µL of 6 N $H_2SO_4$ was added to the 100 µL sample to inactivate the enzymes immediately. Additionally, 240 µL of distilled water was mixed with the sample, and the aggregate enzymes were removed by centrifugation at 13,000×g. Formate production was quantified by HPLC (1260, Agilent, CA, USA) equipped with a diode-array detector and an Aminex HPX-87H column (BIO-RAD, CA, USA) with a mobile phase of 5 µM $H_2SO_4$ at a flow rate of 0.6 mL/min. The retention time of formate was 13.010 min. The formate concentration was calculated using a formate calibration curve (FIG. 5).

3. Results

3.1 Preparation of ReSH and RcFDH

ReSH and RcFDH were expressed in *R. eutropha* and *E. coli*, respectively. These were purified using affinity resins, as described in the Materials and methods.

Five bands of purified ReSH subunits were observed, which matched with the expected molecular weights (HoxF, 68,110 Da; HoxH, 54,863 Da; HoxU, 26,173 Da; HoxY, 22,881 Da; HoxI, 18,567 Da) (FIG. 2A).

Three bands of purified RcFDH subunits were observed, which were consistent with the expected molecular weights (FdsA, 104,466 Da; FdsB, 52,699 Da; FdsG, 17,304 Da) (FIG. 2B).

Figures 6A, 6B, 6C:
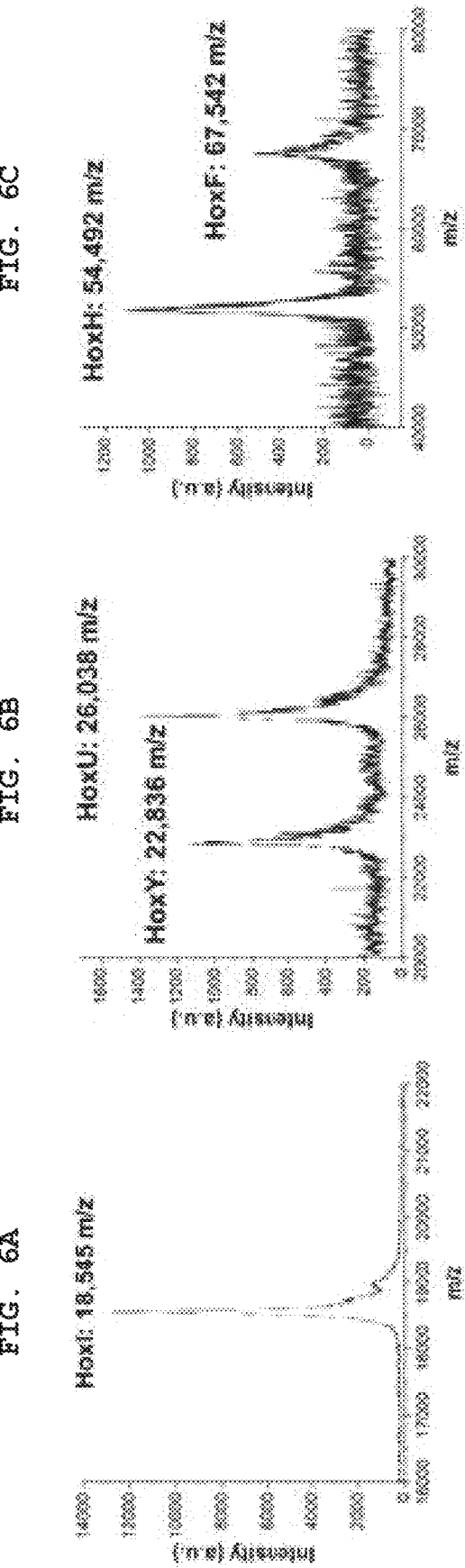
Figure 6E:
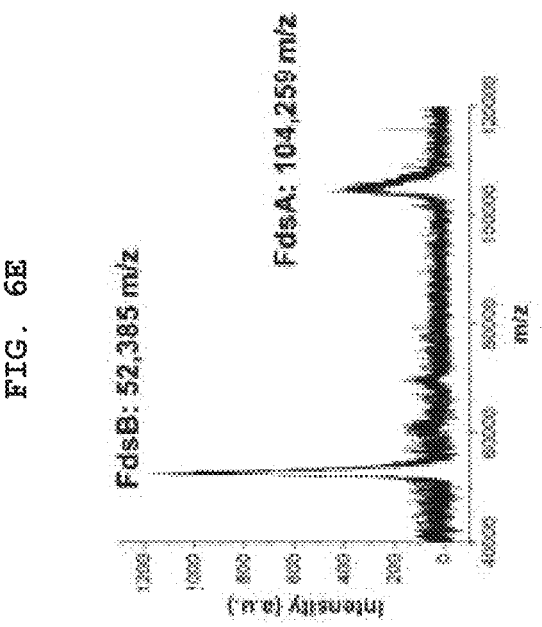
Figure 6D:
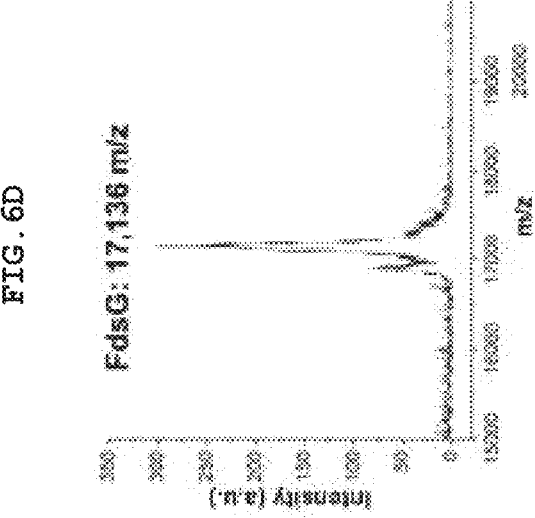

Both enzymes showed high purity. The identity of the purified enzymes was confirmed by MALDI-TOF mass spectrometry. The experimentally determined masses of ReSH subunits were 67,542, 54,492, 26,038, 22,836 and 18,545 m/z, which matched well with the expected masses (68,111, 54,864, 26,174, 22,882 and 18,568 m/z, respectively) with less than 1% deviation (FIGS. 6A, 6B and 6C). The experimentally determined masses of RcFDH subunits were 104,259, 52,385 and 17,136 m/z, which matched well with the expected masses (104,467, 52,700 and 17,305 m/z, respectively) with less than 1% deviation (FIGS. 6D and 6E).

These results showed that the purified ReSH and RcFDH were successfully prepared.

3.2 Enzyme Kinetics in the Presence or Absence of $O_2$

Figures 3A, 3B:
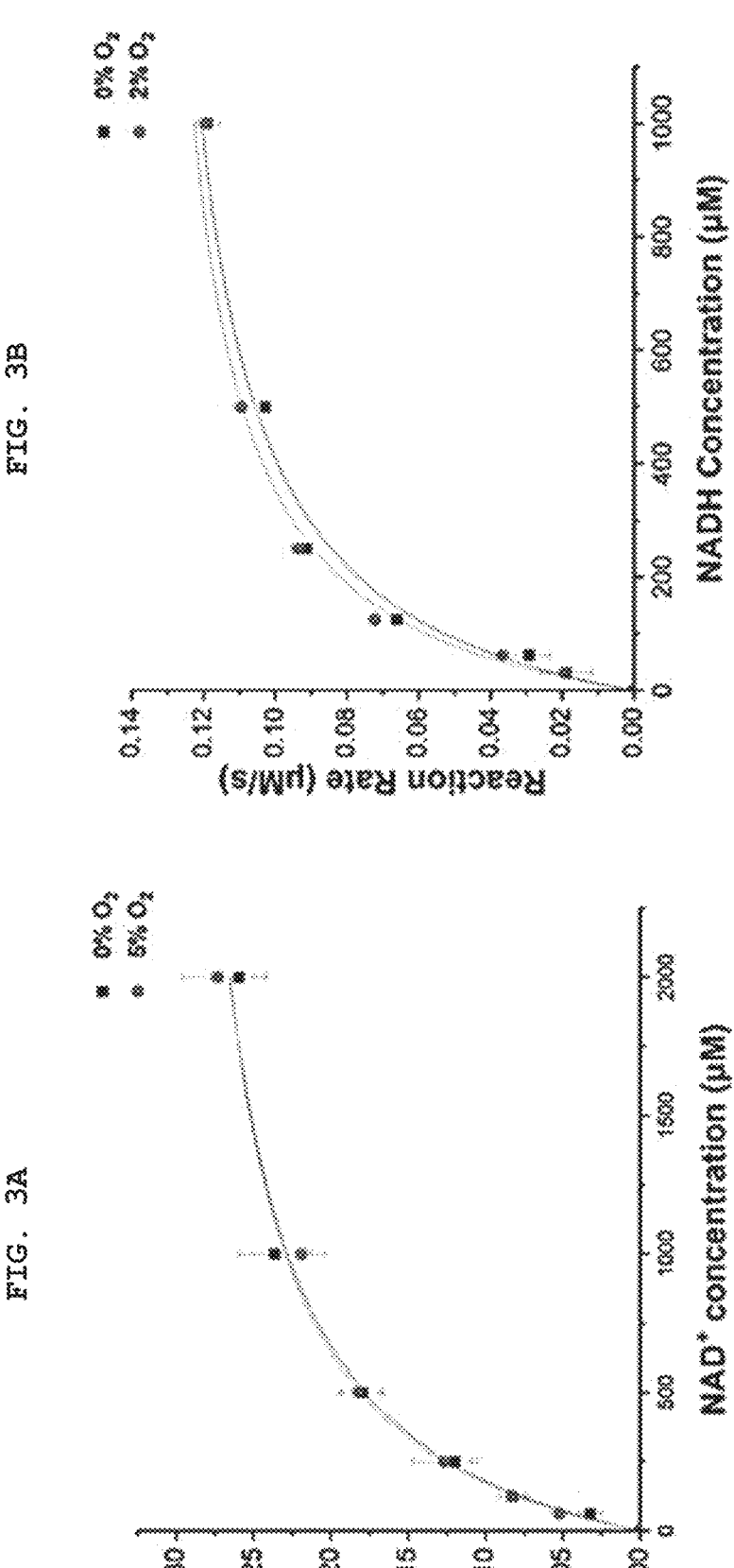
FIG. 3A shows results of kinetic analysis for $NAD^+$-dependent $H_2$ oxidation of ReSH in the presence or absence of $O_2$.
FIG. 3B shows results of kinetic analysis for Nicotinamide adenine dinucleotide (NADH)-dependent $CO_2$ reduction of RcFDH in the presence or absence of $O_2$.

The present inventor investigated the enzymatic activities of ReSH and RcFDH in the presence or absence of $O_2$. The $NAD^+$-dependent $H_2$ oxidation reaction rate by ReSH was measured, and the Michaelis-Menten curve was fitted to calculate the kinetic parameters using Origin 2022 program (FIG. 3A). Both $k_{cat}$ and $K_m$ values of ReSH showed an insignificant difference under the 0% and 5% $O_2$ conditions (Table 1). Similarly, the NADH-dependent $CO_2$ reduction reaction rate by RcFDH was measured, and the Michaelis-Menten curve was fitted to calculate the kinetic parameters (FIG. 3B). Likewise, $k_{cat}$ and $K_m$ values of RcFDH showed an insignificant difference between the 0% and 2% $O_2$ conditions (Table 2). These results show that the purified ReSH and RcFDH retained the enzymatic activity at least under less than 2% $O_2$.

TABLE 1

| $O_2$ concentration (%) | $k_{cat}(s^{-1})$ | $K_m$(mM)($NAD^+$) |
|---|---|---|
| 0 | 39.7 ± 1.5 | 0.393 ± 0.041 |
| 5 | 39.2 ± 1.3 | 0.364 ± 0.033 |

TABLE 2

| $O_2$ concentration (%) | $k_{cat}(s^{-1})$ | $K_m$(mM)(NADH) |
|---|---|---|
| 0 | 0.703 ± 0.043 | 0.166 ± 0.030 |
| 2 | 0.699 ± 0.035 | 0.141 ± 0.022 |

3.3 Cascade Reaction Condition Control

Figure 7:
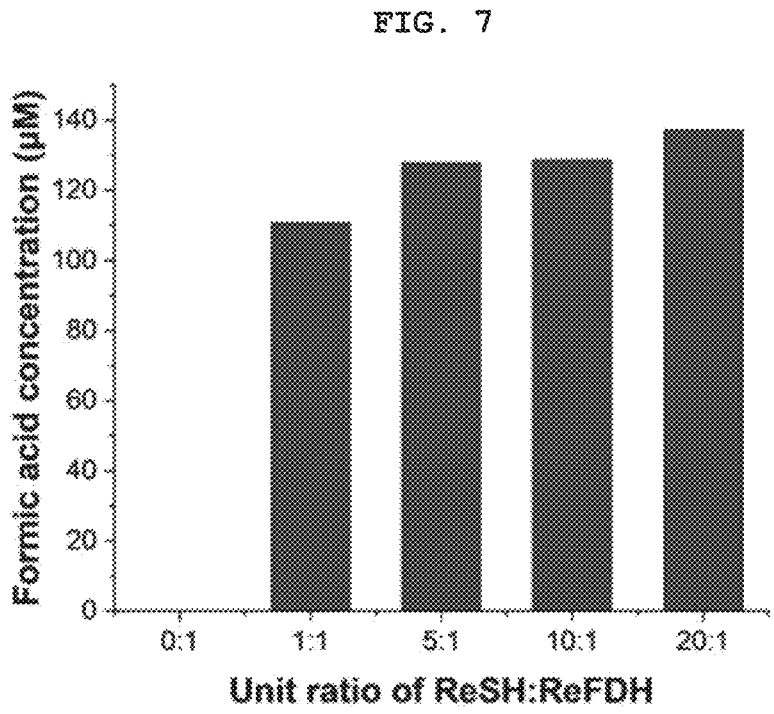
FIG. 7 shows concentrations of formic acid produced after 1 hour at different ratios of ReSH:RcFDH.

The present inventor determined the $NAD^+$, ReSH and RcFDH contents for the cascade reaction of ReSH and RcFDH. Due to the relatively low $k_{cat}$ value (Tables 1 and 2), the rate-determining step was the $CO_2$ reduction by RcFDH. Because the reaction rate of RcFDH was saturated at NADH concentrations above 1 mM (FIG. 3B), the $NAD^+$ concentration was determined to be 1 mM. For the continuous $CO_2$ reduction by RcFDH, the concentration of ReSH was determined to maintain a state in which all $NAD^+$ was reduced to NADH. The concentration of RcFDH was fixed at 0.08 U/mL, and the amount of ReSH was adjusted to 0, 0.08, 0.8 and 1.6 U/mL (U/mL ratio of ReSH:RcFDH=0:1, 1:1, 5:1, 10:1, 20:1). Reaction solutions were placed in a 20 mL sealing vial, and 10 mL/min $CO_2$ and 10 mL/min $H_2$ were injected for 1 h simultaneously, after which formate was measured (FIG. 7). Formate production was not observed in the reaction solution without ReSH. In contrast, substantial formate production was observed in the reaction solution with the three components (ReSH, RcFDH and NAD$^+$). Formate production was saturated in a ratio of above 5:1. At higher ReSH concentrations, NAD$^+$ was immediately converted to NADH through H$_2$ oxidation. Based on this result, the cascade reaction content was set to 1 mM NAD$^+$, and the U/mL ratio of ReSH:RcFDH was set to 20:1.

3.4 Formate Production Under O$_2$ Conditions

Figure 4B:
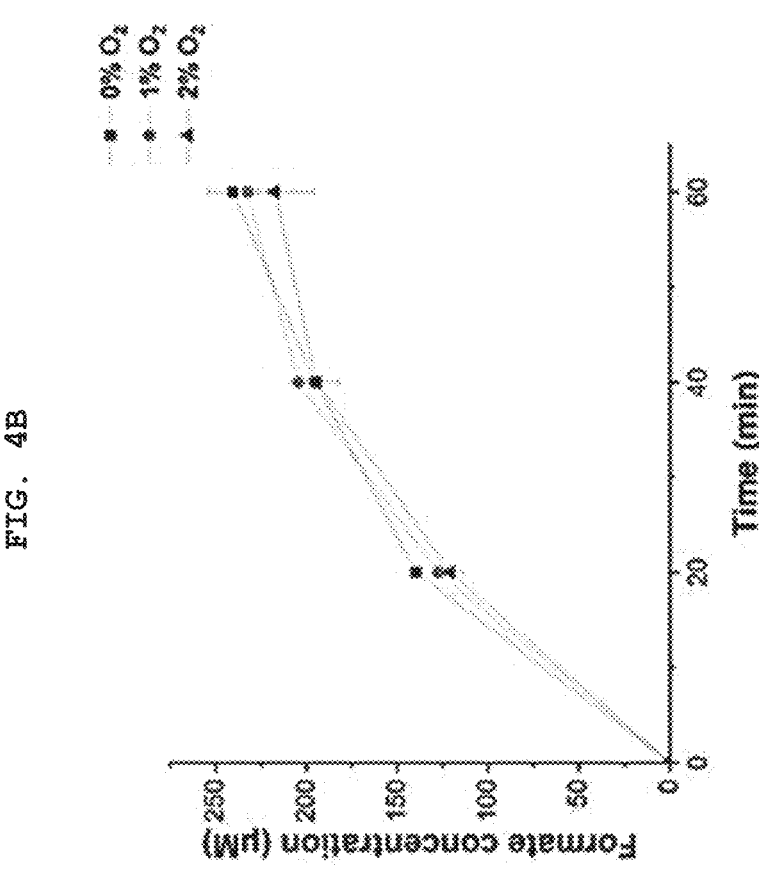
FIGS. 4A and 4B show amounts of NADH and conversion of $H_2$ and $CO_2$ into formate over time by the $NAD^+$-dependent ReSH and RcFDH cascade reactions.
Figure 4A:
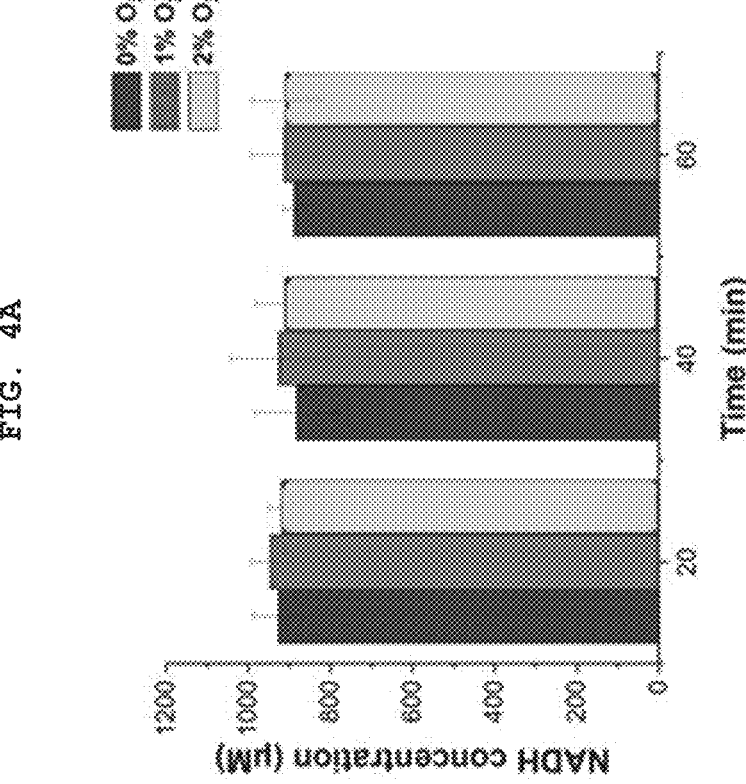
Figure 8:
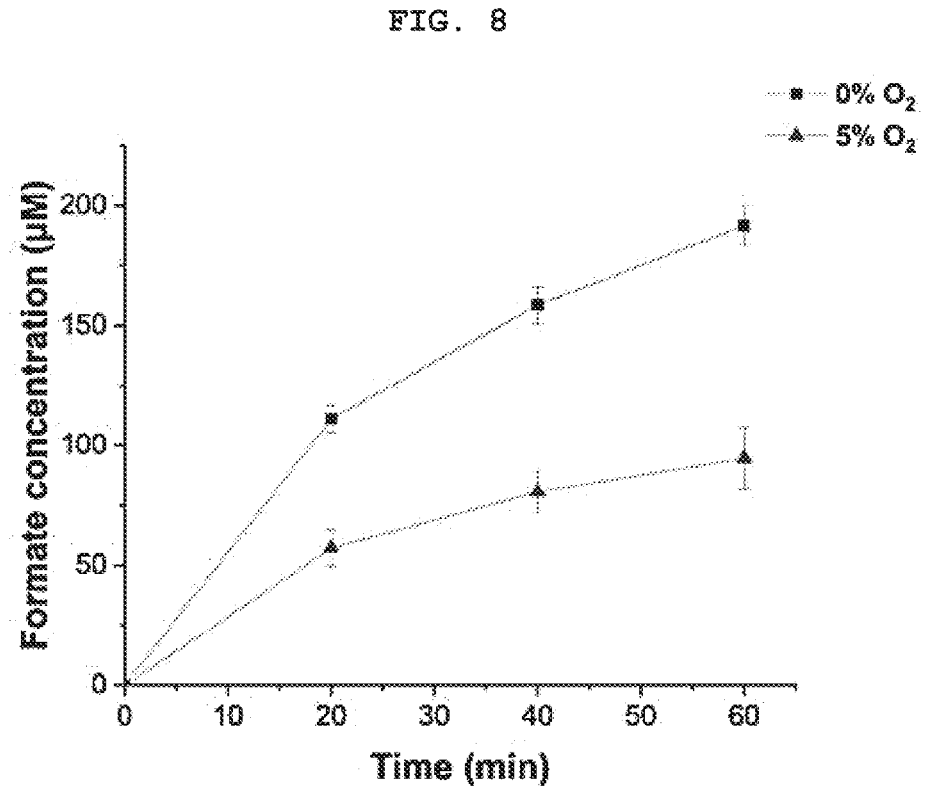
FIG. 8 shows concentrations of $H_2$ and $CO_2$ converted into formate by the $NAD^+$-dependent ReSH and RcFDH cascade reactions under 0%, and 5% $O_2$.

The present inventor demonstrated that H$_2$ and CO$_2$ were converted into formate under 0% to 2% O$_2$ conditions. ReSH, RcFDH and 1 mM NAD$^+$ were mixed and placed in a 20 mL sealing vial. Changes in the concentrations of NADH and formate over time were investigated when O$_2$ (at a controlled concentration), H$_2$ and CO$_2$ were simultaneously and continuously injected into the vial. During the injection of the gases, under all O$_2$ conditions between 0% and 2%, NAD$^+$ was reduced to NADH and maintained at 1 mM by H$_2$ oxidation of ReSH (FIG. 4A). Furthermore, the formate concentration was increased continuously (FIG. 4B) due to the CO$_2$ reduction of RcFDH. Approximately 230 μM of formate was produced after 1 h, which showed a statistically insignificant difference at 0, 1 or 2% O$_2$ conditions (p>0.05). In order to investigate the O$_2$-tolerance limit of the system, the present inventor tested the formate production at a higher concentration of O$_2$ (FIG. 8). As compared to 0%, a substantial reduction in formate production at 5% O$_2$ was observed by the present inventor. Therefore, in the specific enzyme systems chosen by the present inventor, the O$_2$-tolerance limit was between 2 and 5%. The O$_2$-tolerance of both H$_2$ase and FDH is attributed to the reduction of O$_2$ bound to the active site of enzymes, leading to the reactivation of active site. Therefore, the present inventor speculated that the substantial loss of enzymatic activities at 5% O$_2$ results from that O$_2$ binding to the active site is more favorable than O$_2$ reduction at the active site. These results demonstrate, as hypothesized, the plausibility of a cascade reaction using ReSH and RcFDH, even in the presence of O$_2$.

4. Conclusions

The present inventor demonstrated the conversion of H$_2$ and CO$_2$ into formate using an NAD$^+$-dependent cascade reaction of O$_2$-tolerant H$_2$ase and O$_2$-tolerant FDH in the presence of O$_2$.

REFERENCE TO AN ELECTRONIC SEQUENCE LISTING

A sequence listing electronically submitted on Dec. 21, 2023 as a XML file named 20231221_LC0592321_TU_SEQ.XML, created on Dec. 21, 2023 and having a size of 13,037 bytes, is incorporated herein by reference in its entirety.

---

What is claimed is:

1. A process for producing formate, the process comprising:

preparing a mixed enzyme by mixing hydrogenase ($H_2$ase) with oxygen tolerance and formate dehydrogenase (FDH) with oxygen tolerance; and mixing the mixed enzyme and a gas including $H_2$, $CO_2$ and Nicotinamide adenine dinucleotide phosphate ($NAD^+$), wherein the hydrogenase ($H_2$ase) with oxygen tolerance comprises the amino acid sequence of SEQ ID NO: 1, wherein the formate dehydrogenase (FDH) with oxygen tolerance comprises the amino acid sequence of SEQ ID NO: 6, wherein the gas including $H_2$ contains 5% or less of $O_2$.

2. The process of claim 1, wherein the gas including $H_2$ is obtained from any one source selected from the group consisting of byproduct hydrogen incidentally generated in a process of a petrochemical or steel industry, gas generated from plastic or solid waste, coke, naphtha, volcanic gas, mineral water, coal gas, solar heat, algae emission, biomass, natural gas, fossil fuel, coal, peat, petroleum and natural gasoline.

3. The process of claim 1, wherein the hydrogenase is obtained from *Ralstonia eutropha*.

4. The process of claim 1, wherein the formate dehydrogenase is obtained from *Rhodobacter capsulatus*.

5. The process of claim 1, wherein the gas including H2 contains 2% or less of $O_2$.

6. The process of claim 1, wherein the hydrogenase and the formate dehydrogenase are mixed in a ratio of 5 to 25:1.

* * * * *

```
SEQUENCE LISTING

Sequence total quantity: 10
SEQ ID NO: 1              moltype = AA   length = 614
FEATURE                  Location/Qualifiers
source                   1..614
                         mol_type = protein
                         organism = Ralstonia sp.
SEQUENCE: 1
MASWSHPQFE KGADSRITTI LERYRSDRTR LIDILWDVQH EYGHIPDAVL PQLGAGLKLS  60
PLDIRETASF YHFFLDKPSG KYRIYLCNSV IAKINGYQAV REALERETGI RFGETDPNGM  120
FGLFDTPCIG LSDQEPAMLI DKVVFTRLRP GKITDIIAQL KQGRSPAEIA NPAGLPSQDI  180
AYVDAMVESN VRTKGPVFFR GRTDLRSLLD QCLLLKPEQV IETIVDSRLR GRGGAGFSTG  240
LKWRLCRDAE SEQKYVICNA DEGEPGTFKD RVLLTRAPKK VFVGMVIAAY AIGCRKGIVY  300
LRGEYFYLKD YLERQLQELR EDGLLGRAIG GRAGFDFDIR IQMGAGAYIC GDESALIESC  360
EGKRGTPRVK PPFPVQQGYL GKPTSVNNVE TFAAVSRIME EGADWFRAMG TPDSAGTRLL  420
SVAGDCSKPG IYEVEWGVTL NEVLAMVGAR DARAVQISGP SGECVSVAKD GERKLAYEDL  480
SCNGAFTIFN CKRDLLEIVR DHMQFFVEES CGICVPCRAG NVDLHRKVEW VIAGKACQKD  540
LDDMVSWGAL VRRTSRCGLG ATSPKPILTT LEKFPEIYQN KLVRHEGPLL PSFDLDTALG  600
GYEKALKDLE EVTR                                                   614

SEQ ID NO: 2              moltype = AA   length = 234
FEATURE                  Location/Qualifiers
source                   1..234
                         mol_type = protein
                         organism = Ralstonia sp.
SEQUENCE: 2
MSIQITIDGK TLTTEEGRTL VDVAAENGVY IPTLCYLKDK PCLGTCRVCS VKVNGNVAAA  60
CTVRVSKGLN VEVNDPELVD MRKALVEFLF AEGNHNCPSC EKSGRCQLQA VGYEVDMMVS  120
RFPYRFPVRV VDHASEKIWL ERDRCIFCQR CVEFIRDKAS GRKIFSISHR GPESRIEIDA  180
ELANAMPPEQ VKEAVAICPV GTILEKRVGY DDPIGRRKYE IQSVRARALE GEDK        234

SEQ ID NO: 3              moltype = AA   length = 209
FEATURE                  Location/Qualifiers
source                   1..209
                         mol_type = protein
                         organism = Ralstonia sp.
SEQUENCE: 3
MRAPHKDEIA SHELPATPMD PALAANREGK IKVATIGLCG CWGCTLSFLD MDERLLPLLE  60
KVTLLRSSLT DIKRIPERCA IGFVEGGVSS EENIETLEHF RENCDILISV GACAVWGGVP  120
AMRNVFELKD CLAEAYVNSA TAVPGAKAVV PFHPDIPRIT TKVYPCHEVV KMDYFIPGCP  180
PDGDAIFKVL DDLVNGRPFD LPSSINRYD                                   209

SEQ ID NO: 4              moltype = AA   length = 488
FEATURE                  Location/Qualifiers
```

```
source                      1..488
                            mol_type = protein
                            organism = Ralstonia sp.
SEQUENCE: 4
MSRKLVIDPV TRIEGHGKVV VHLDDDNKVV DAKLHVVEFR GFEKFVQGHP FWEAPMFLQR   60
ICGICFVSHH LCGAKALDDM VGVGLKSGIH VTPTAEKMRR LGHYAQMLQS HTTAYFYLIV  120
PEMLFGMDAP PAQRNVLGLI EANPDLVKRV VMLRKWGQEV IKAVFGKKMH GINSVPGGVN  180
NNLSIAERDR FLNGEEGLLS VDQVIDYAQD GLRLFYDFHQ KHRAQVDSFA DVPALSMCLV  240
GDDDNVDYYH GRLRIIDDDK HIVREFDYHD YLDHFSEAVE EWSYMKFPYL KELGREQGSV  300
RVGPLGRMNV TKSLPTPLAQ EALERFHAYT KGRTNNMTLH TNWARAIEIL HAAEVVKELL  360
HDPDLQKDQL VLTPPPNAWT GEGVGVVEAP RGTLLHHYRA DERGNITFAN LVVATTQNNQ  420
VMNRTVRSVA EDYLGGHGEI TEGMMNAIEV GIRAYDPCLS CATHALGQMP LVVSVFDAAG  480
RLIDERAR                                                          488

SEQ ID NO: 5              moltype = AA  length = 167
FEATURE                   Location/Qualifiers
source                    1..167
                          mol_type = protein
                          organism = Ralstonia sp.
SEQUENCE: 5
MKEQEIDRIA TMIYEAPLGE YIGRDGAAIL AEHAAEARLL KGDEFLYRRG DVTSSFYIVT   60
DGRLALVREK TNERTAPIVH VLEKGDLVGE LGFIDQTPHS LSVRALGDAA VLSFSAESIK  120
PLITEHPELI FNFMRAVIKR VHHVVVTVGE HERELQEYIS TGGRGRG                167

SEQ ID NO: 6              moltype = AA  length = 166
FEATURE                   Location/Qualifiers
source                    1..166
                          mol_type = protein
                          organism = Rhodobacter capsulatus
SEQUENCE: 6
MGGSWSHPQF EKGMASMTDT ARLRAILAAH RGREGALLPI LHDVQAAFGF IPEDAYAPIA   60
ADLGLTRAEV AGVVGFYHDF RKAPAGRHVI KLCRAEACQA MGMDAVQARL ESALGLRLGD  120
SSEAVTLEAV YCLGLCACAP AAMVDDRLVG RLDAAAVAGI VAELGA                166

SEQ ID NO: 7              moltype = AA  length = 500
FEATURE                   Location/Qualifiers
source                    1..500
                          mol_type = protein
                          organism = Rhodobacter capsulatus
SEQUENCE: 7
MKIWLPCDAA AKACGAEAVL AALRLEAEKR GGALDIARNG SRGMIWLEPL LEVETPAGRI   60
GFGPMTPADV PALFDALESH PKALGLVEEI PFFKRQTRLT FARCGRIEPL SLAQFAAAEG  120
WAGLRKALKM TPAEVVEEVL ASGLRGRGGA GFPTGIKWRT VAAAQADQKY IVCNVDEGDS  180
GSFADRMLIE GDPFCLVEGM AIAGHAVGAT RGYVYIRSEY PDAIAVMRAA IAMAKPFLAE  240
AGFEMEVRVG AGAYVCGEET SLLNSLEGKR GTVRAKPPLP ALKGLFGKPT VVNNLLSLAA  300
VPWIIAHGAK AYESFGMDRS RGTIPLQIGG NVKRGGLFET GFGITLGELV EDICGGTASG  360
RPVKAVQVGG PLGAYHPVSD YHLPFCYEQF AGQGGLVGHA GLVVHDDTAD MLKLARFAME  420
FCAIESCGTC TPCRIGAVRG VEVIDRIAAG DASAMPLLDD LCQTMKLGSL CALGGFTPYP  480
VQSAIRHFPA DFPCAREAAE                                             500

SEQ ID NO: 8              moltype = AA  length = 958
FEATURE                   Location/Qualifiers
source                    1..958
                          mol_type = protein
                          organism = Rhodobacter capsulatus
SEQUENCE: 8
MKDLIIPPLD WTQDMGTPKR EGAPVHLTID GVEVTVPAGT SVLRAAAEAG ISIPKLCATD   60
NVEPVGSCRL CMVEIEGMRG TPTSCTTPVA PGMRVHTQTP QLQKLRRGVM ELYISDHPLD  120
CLTCAANGDC ELQDMAGAVG LREVRYQAKD THFARRDATG PNPRYIPKDN SNPYFSYDPA  180
KCIVCMRCVR ACEEVQGTFA LTVMGRGFDA RISPAAPDFL SSDCVSCGAC VQACPTATLV  240
EKSVERIGTP ERKVVTTCAY CGVGCSFEAH MLGDQLVRMV PWKGGAANRG HSCVKGRFAY  300
GYATHQDRIL KPMIRDKITD PWREVNWTEA LDFTATRLRA LRDSHGADAL GVITSSRCTN  360
EETYLVQKLA RAVFGTNNTD TCARVCHSPT GYGLKQTFGT SAGTQDFDSV EETDLALVIG  420
ANPTDGHPVF ASRLRKRLRA GAKLIVVDPR RIDLLNTPHR GEAWHLQLKP GTNVAVMTAM  480
AHVIVTEQIF DKRFIGDRCD WDEWADYAEF VANPEYAPEA VESLTGVPAG LLRQAARAYA  540
AAPNAAIYYG LGVTEHSQGS TTVIAIANLA MMTGNIGRPG VGVNPLRGQN NVQGSCDMGS  600
FPHEFPGYRH VSDDATRGLF ERTWGVTLSS EPGLRIPNML DAAVEGRFKA LYVQGEDILQ  660
SDPDTRHVSA GLAAMDLVIV HDLFLNETAN YAHVFLPGST FLEKDGTFTN AERRINRVRR  720
VMAPKAGFAD WEVTQMLANA LGAGWHYTHP SEIMAEIAAT TPGFAAVTYE MLDARGSVQW  780
PCNEKAPEGS PIMHVEGFVR GKGRFIRTAY LPTDEKTGPR FPLLLTTGRI LSQYNVGAQT  840
RRTENTVWHG EDRLEIHPTD AETRGIRDGD WVRLASRAGE TTLRATVTDR VSPGVVYTTF  900
HHPDTQANVV TTDTSDWATN CPEYKVTAVQ VAASNGPSDW QQDYAAQAAA ARRIEAAE    958

SEQ ID NO: 9              moltype = DNA  length = 44
FEATURE                   Location/Qualifiers
source                    1..44
                          mol_type = other DNA
                          organism = synthetic construct
SEQUENCE: 9
```

-continued

```
gccacccgca gttcgaaaaa ggtatggcta gcatgacgga tacc                    44

SEQ ID NO: 10          moltype = DNA   length = 44
FEATURE                Location/Qualifiers
source                 1..44
                       mol_type = other DNA
                       organism = synthetic construct
SEQUENCE: 10
cgaactgcgg gtggctccaa gaacccccca tggtttattc ctcc                    44
```